(12) United States Patent
Hetzel

(10) Patent No.: US 10,688,286 B2
(45) Date of Patent: Jun. 23, 2020

(54) DEVICES AND METHODS FOR SECURING SURGICAL GUIDE WIRES

(71) Applicant: Secure Surgical Inc., Asheville, NC (US)

(72) Inventor: David J. Hetzel, Asheville, NC (US)

(73) Assignee: SECURE SURGICAL INC, Asheville, NC (US)

( * ) Notice: Subject to any disclaimer, the term of this patent is extended or adjusted under 35 U.S.C. 154(b) by 199 days.

(21) Appl. No.: 15/267,935

(22) Filed: Sep. 16, 2016

(65) Prior Publication Data

US 2017/0079635 A1    Mar. 23, 2017

Related U.S. Application Data

(60) Provisional application No. 62/219,848, filed on Sep. 17, 2015.

(51) Int. Cl.
*A61M 25/00*    (2006.01)
*A61M 25/09*    (2006.01)

(52) U.S. Cl.
CPC ... *A61M 25/09* (2013.01); *A61M 2025/09125* (2013.01)

(58) Field of Classification Search
CPC ........ A61M 25/09; A61M 2025/09125; A61M 2025/09116; A61M 25/02; A61M 2025/026–0293
See application file for complete search history.

(56) References Cited

U.S. PATENT DOCUMENTS

| | | | | |
|---|---|---|---|---|
| 5,304,184 A | * | 4/1994 | Hathaway | A61B 17/0057 606/144 |
| 6,096,009 A | * | 8/2000 | Windheuser | A61M 25/0097 24/339 |
| 2002/0032432 A1 | * | 3/2002 | Nash | A61M 25/00 604/533 |
| 2005/0182420 A1 | * | 8/2005 | Schulte | A61N 1/0539 606/130 |
| 2010/0010475 A1 | * | 1/2010 | Teirstein | A61M 25/02 604/528 |
| 2012/0078087 A1 | | 3/2012 | Curry et al. | |
| 2013/0096505 A1 | * | 4/2013 | Urmey | A61M 25/013 604/165.02 |
| 2014/0066754 A1 | | 3/2014 | Sing et al. | |
| 2014/0276441 A1 | * | 9/2014 | Cohen | A61M 25/02 604/180 |
| 2015/0011834 A1 | * | 1/2015 | Ayala | A61B 17/0218 600/208 |
| 2017/0079635 A1 | | 3/2017 | Hetzel et al. | |

* cited by examiner

*Primary Examiner* — Charles A Marmor, II
*Assistant Examiner* — David Joseph Fernandez-Fidalgo
(74) *Attorney, Agent, or Firm* — Casimir Jones, S.C.; Tanya Arenson

(57) ABSTRACT

Provided herein are devices and methods for securing surgical guide wires. In particular, provided herein are devices for securing radiologically located guide wires prior to surgery (e.g., lumpectomy).

17 Claims, 8 Drawing Sheets

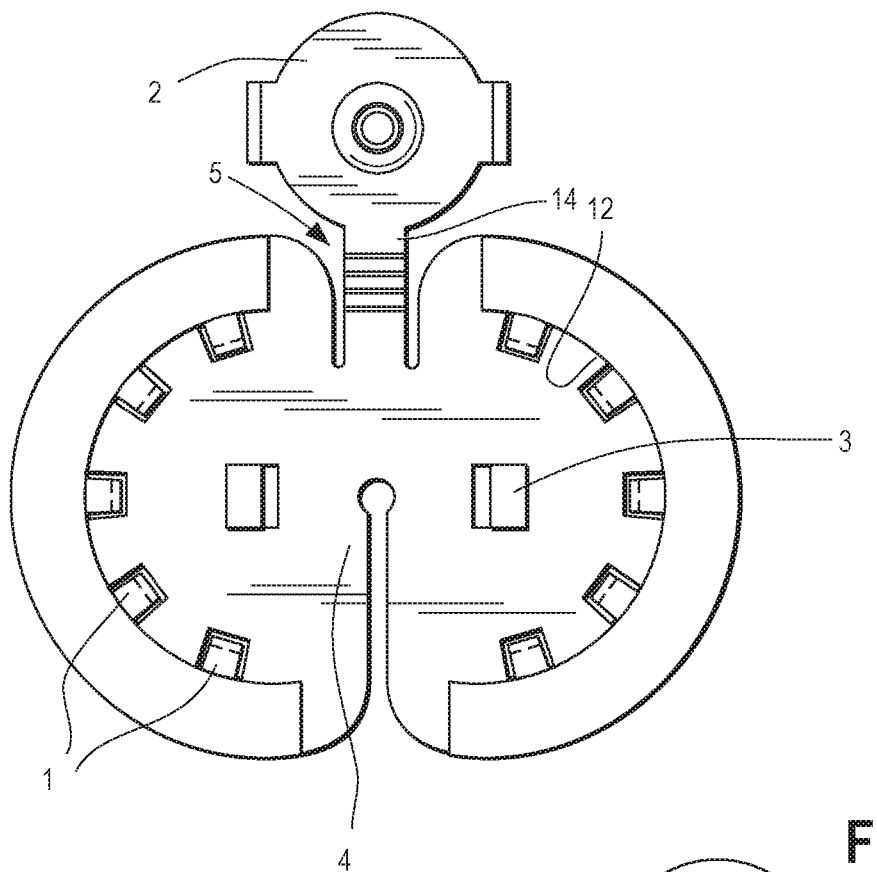
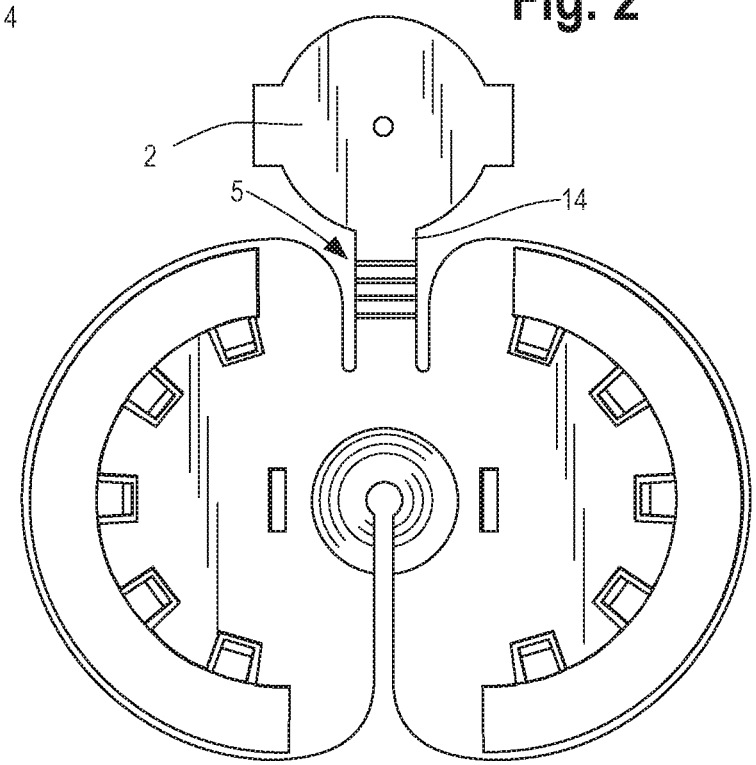

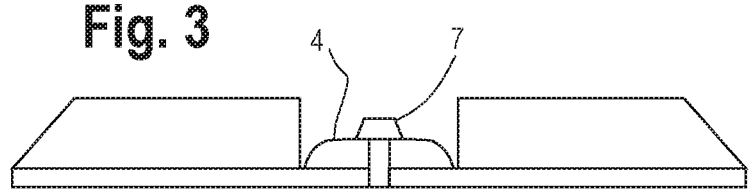
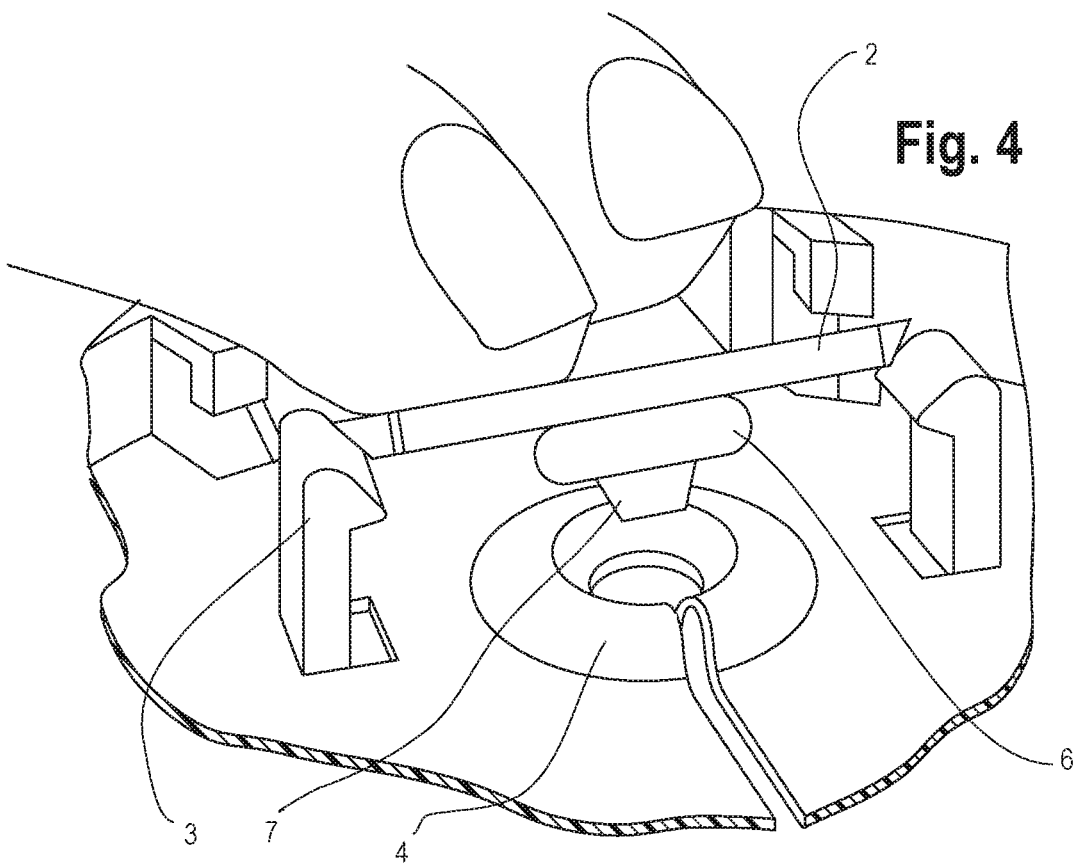
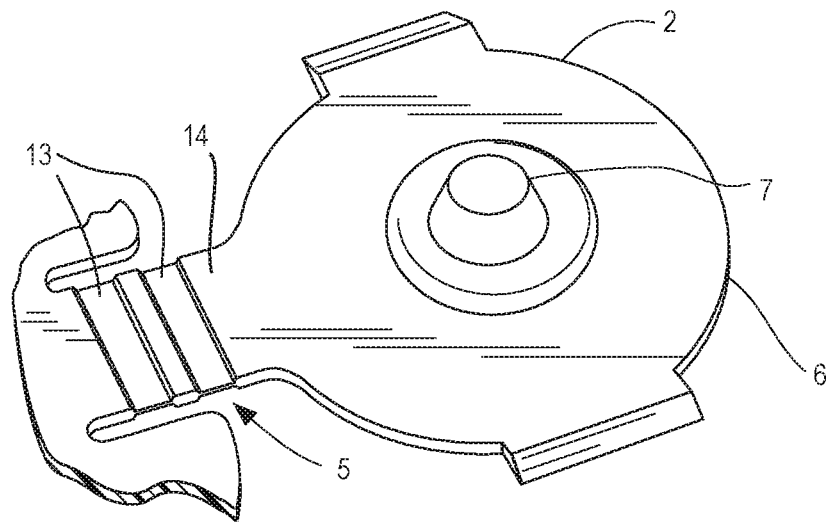

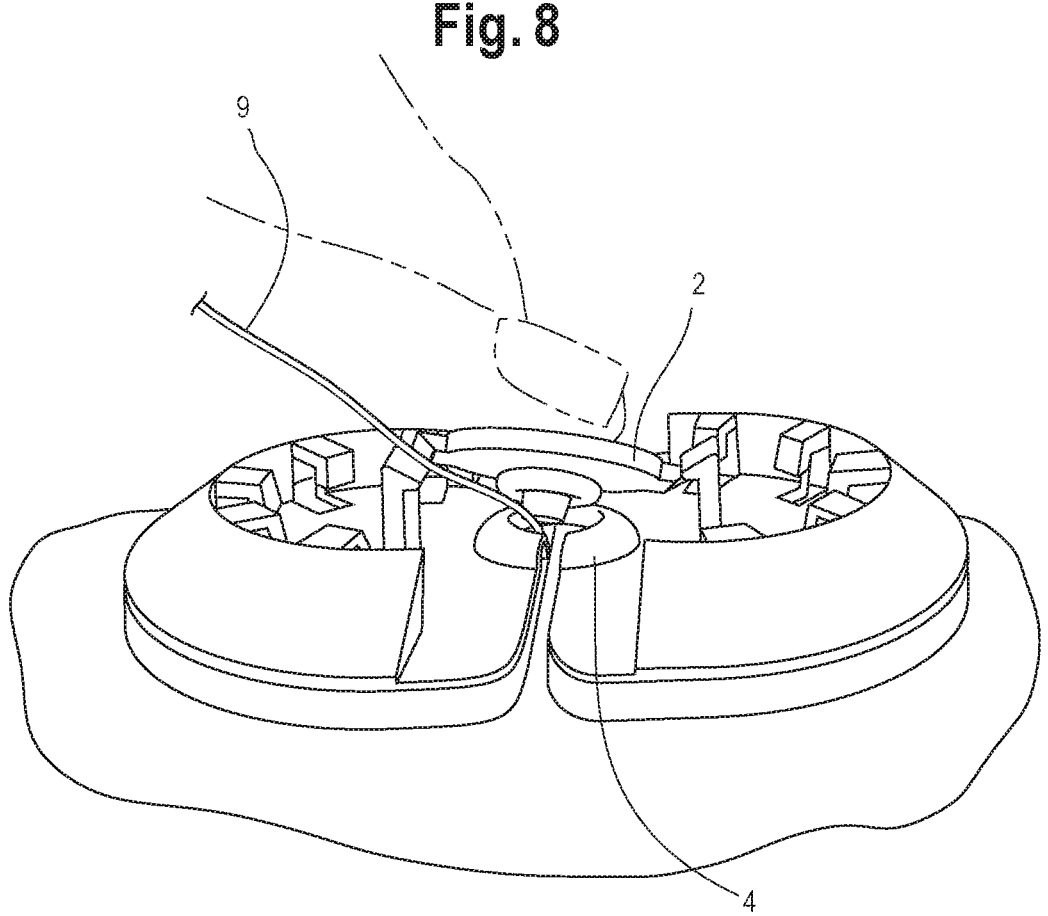

DEVICES AND METHODS FOR SECURING SURGICAL GUIDE WIRES

This application claims priority to provisional application 62/219,848, filed Sep. 17, 2015, which is herein incorporated by reference in its entirety.

FIELD OF THE INVENTION

Provided herein are devices and methods for securing surgical guide wires. In particular, provided herein are devices for securing radiologically located guide wires prior to surgery (e.g., lumpectomy).

BACKGROUND OF THE INVENTION

Needle localizations are commonly performed by radiologists before excisional biopsy of non-palpable breast lesions, using one of a number of commercially available needle and wire systems such as the Kopans wire. An imaging device such as an ultrasound probe, mammogram, CT, or MM is used to place the wire in or around the abnormal area. The surgeon then uses this wire as a guide to find and remove the tumor during surgery. The wire will also be removed during surgery.

After wire localization, patients then have to travel, often in a car to the hospital or outpatient surgery center. During transit, it is important that wires do not move or become dislodged. If the wires are not properly localized, a delay in surgery and costly replacement of the wires is often required.

The long, protruding wire is difficult to manage. Currently, wires are typically covered with a bandage and/or medical tape, which does not provide adequate protection against wires dislodging. Improved methods of securing guide wires are needed.

SUMMARY OF THE INVENTION

Provided herein are devices and methods for securing surgical guide wires. In particular, provided herein are devices for securing radiologically located guide wires prior to surgery (e.g., lumpectomy).

For example, in some embodiments, provided herein is a guide wire securing device, comprising: one or more of a wire conformation, retention, and management component (e.g., one or more of wire hooks and/or a grooved track), a locking component (e.g., comprising one or more of a clocking tab insertion component, a locking tab, a connecting arm incorporating a hinge (e.g., living hinge), a wire insertion groove, a locking clip, and a wire hole, or an attachment component). In some embodiments, the wire insertion groove is Y-shaped. In some embodiments, the locking tab comprises a rubber washer and closing tab. In some embodiments, the attachment component comprises adhesive attached to the back edge of the device. In some embodiments, the adhesive is foam adhesive. In some embodiments, the device is fabricated from a polymeric material.

Further embodiments provide systems and kits comprising the devices described herein and a plurality of guide wires (e.g., surgical guide wires).

Additional embodiments provide a method of securing a guide wire, comprising: a) contacting a guide wire inserted into a body part of a patient with a guide wire securing device, comprising: a wire conformation, retention, and management component, a locking component, and an attachment component; b) inserting the guide wire through the wire retention component of the device; and c) securing the wire using the locking component. In some embodiments, the guide wires are surgical guide wires (e.g., breast cancer guide wires that identify a breast lump or tumor). In some embodiments, the device is securing to the patient using the adhesive component. In some embodiments, the patient is pre-operative. In some embodiments, the device is removed from the patient prior to the patient undergoing surgery (e.g., lumpectomy). In some embodiments, the guide wires protrude from the patient and are long (e.g., approximately 7-22 cm). In some embodiments, the device facilities rapid and easy wrapping and management of the guide wires.

Additional embodiments are described herein.

DESCRIPTION OF THE FIGURES

FIG. 1 shows a top view of exemplary devices of embodiments of the present disclosure.

FIG. 2 shows a back view of exemplary devices of embodiments of the present disclosure.

FIG. 3 shows a side view of exemplary devices of embodiments of the present disclosure.

FIG. 4 shows a close up of the locking area of exemplary devices of embodiments of the present disclosure.

FIG. 5 shows a close up of the locking area of exemplary devices of embodiments of the present disclosure.

FIG. 8 shows an exemplary device of embodiments of the present disclosure with guide wires attached and secured.

DESCRIPTION OF THE INVENTION

Figure 6:
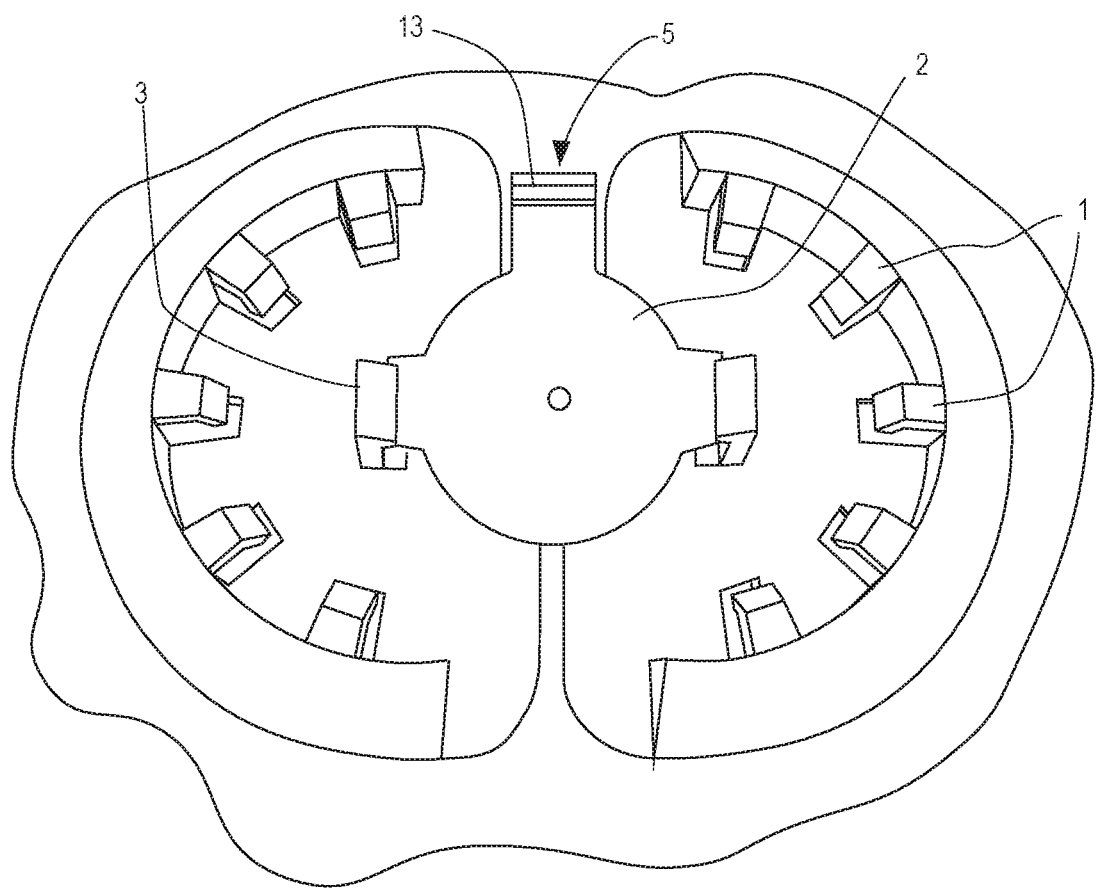
FIG. 6 shows a close up of the inner track for wrapping and securing wires of exemplary devices of embodiments of the present disclosure.

Provided herein are devices and methods for securing surgical guide wires. In particular, provided herein are devices for securing radiologically located guide wires prior to surgery (e.g., lumpectomy).

Embodiments of the present disclosure provide devices and methods that improve over existing methods of securing guide wires after placement. In some embodiments, the present disclosure provides devices that serve to securely lock the wires in place and prevent movement or dislodging of wires. The devices and methods described herein assist the patient and clinicians in managing the wire in a quicker and easier manner than existing technologies.

For example, in some embodiments, provided herein is a guide wire securing device, comprising: one or more of a wire conformation, retention, and management component (e.g., one or more of wire hooks and/or a grooved track), a locking component (e.g., comprising one or more of a clocking tab insertion component, a locking tab, a hinge, a wire insertion groove, a locking clip, and a wire hole, or an attachment component).

As used herein, the term "wire retention and management component" refers to a component of the described devices that serves to secure wires and management the conformation, location, and security of wires (e.g., guide wires). In some embodiments, the wire retention and management component comprises one or more components including, but not limited to, wire hooks, a grooved wire track, and the like.

As used herein, the term "locking component" refers to a component of the devices described herein that locks wires (e.g., wires secured by the "wire retention and management component") in place (e.g., during use of the guide wires). In some embodiments, the locking component comprises one or more components including, but not limited to, a clocking tab insertion component, a locking tab, a hinge, a wire insertion groove, a locking clip, a wire hole, and the like.

The term "living hinge" refers to a hinge (e.g., as described herein) that comprises a plurality (e.g., 1, 2, 3, 4, or more) grooves in a connecting arm that allow the arm to easily bend without breaking. In some embodiments, this allows the locking cap to bend about 180 degrees over and into snapped down or locked position.

Exemplary devices of embodiments of the present disclosure are shown in FIGS. 1-6. FIG. 1 shows a top view of an exemplary device. Shown are wire hooks 1; locking component comprising locking tab 2, locking clip 3, and locking tab insertion component 4; grooved track 12, and a connecting arm 14 incorporating hinge 5. In some embodiments, the hinge is a living hinge. In some embodiments, the living hinge comprises bendable sections 13.

FIG. 2 shows a back view of an exemplary device. Shown are wire hooks 1, locking tab 2, locking clip 3, locking tab insertion component 4, and hinge 5. FIG. 3 shows side view of an exemplary device. Shown are wire hooks 1, locking tab 2, and living hinge 5. FIG. 4 shows a close up of the locking area of an exemplary device. Shown are locking tab 2, locking clip 3, and locking tab insertion component 4. FIG. 5 shows a close up of the locking area of an exemplary device. Shown are locking tab 2, rubber washer 6, and closing tab 7. FIG. 6 shows a close up of the inner track for wrapping and securing wires of an exemplary device. Shown are wire hooks 1, locking tab 2, locking clip 3, and hinge 5.

Figure 7A:
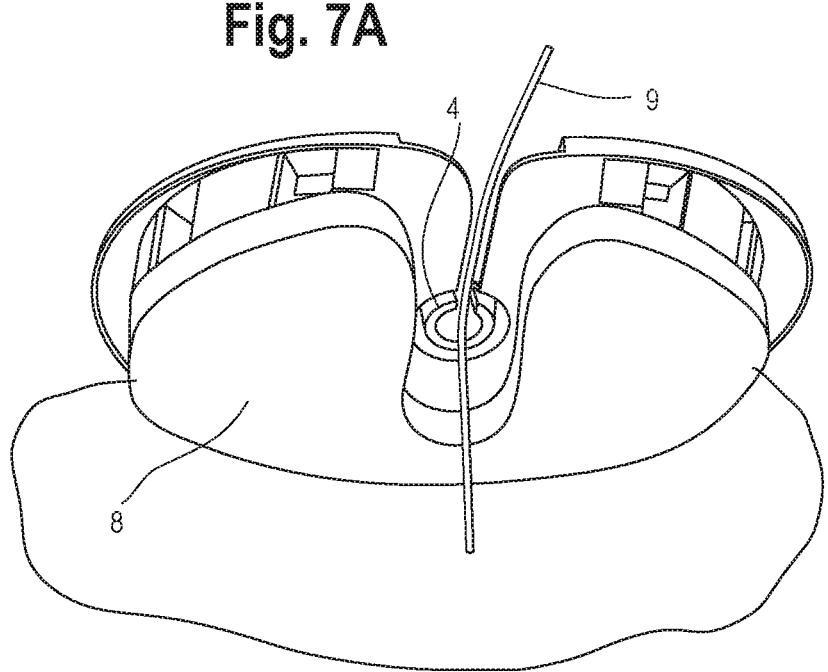
FIGS. 7A and 7B show an exemplary device of embodiments of the present disclosure with guide wires attached.
Figure 7B:
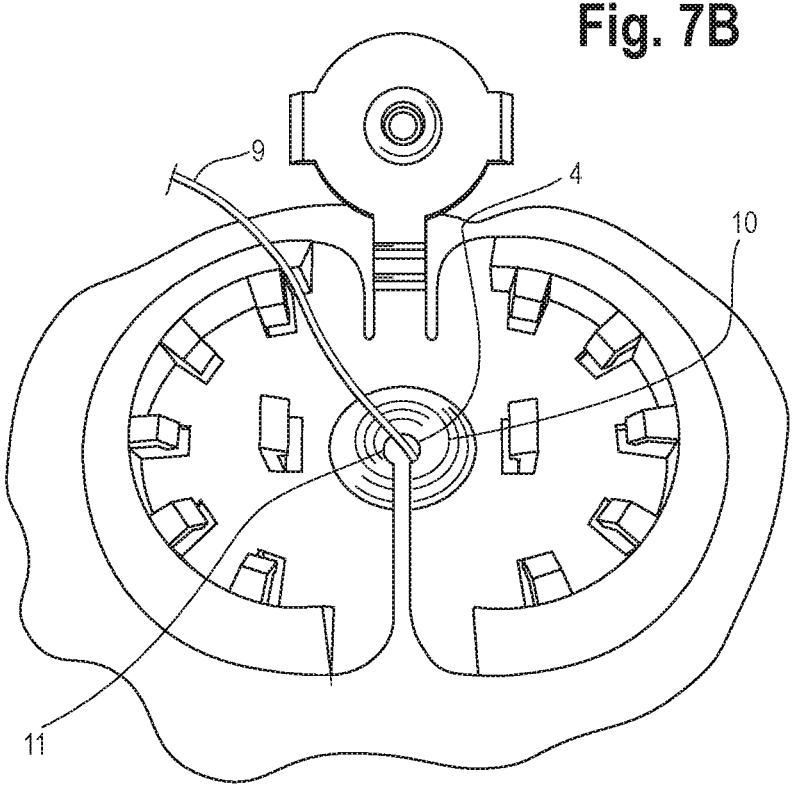

FIGS. 7-11 show exemplary devices in operation. FIG. 7 shows locking tab insertion component 4, optional adhesive and padding 8, and guide wires 9. The locking tab insertion component 4 further comprises a wire insertion groove 11 (e.g., a Y-shaped insertion groove 11) for inserting wire into hole 10. The padding 8 is constructed from any suitable material (e.g., foam). In some embodiments, the padding 8 comprises adhesive to attach the device to the patient's body. The guide wires 9 are inserted through the hole in locking tab insertion component 4. After the guide wire 9 is inserted through the hole 10 in locking tab insertion component 4, the locking tab 2, is closed by inserting into locking tab insertion component 4 as shown in FIG. 8.

Figure 9A:
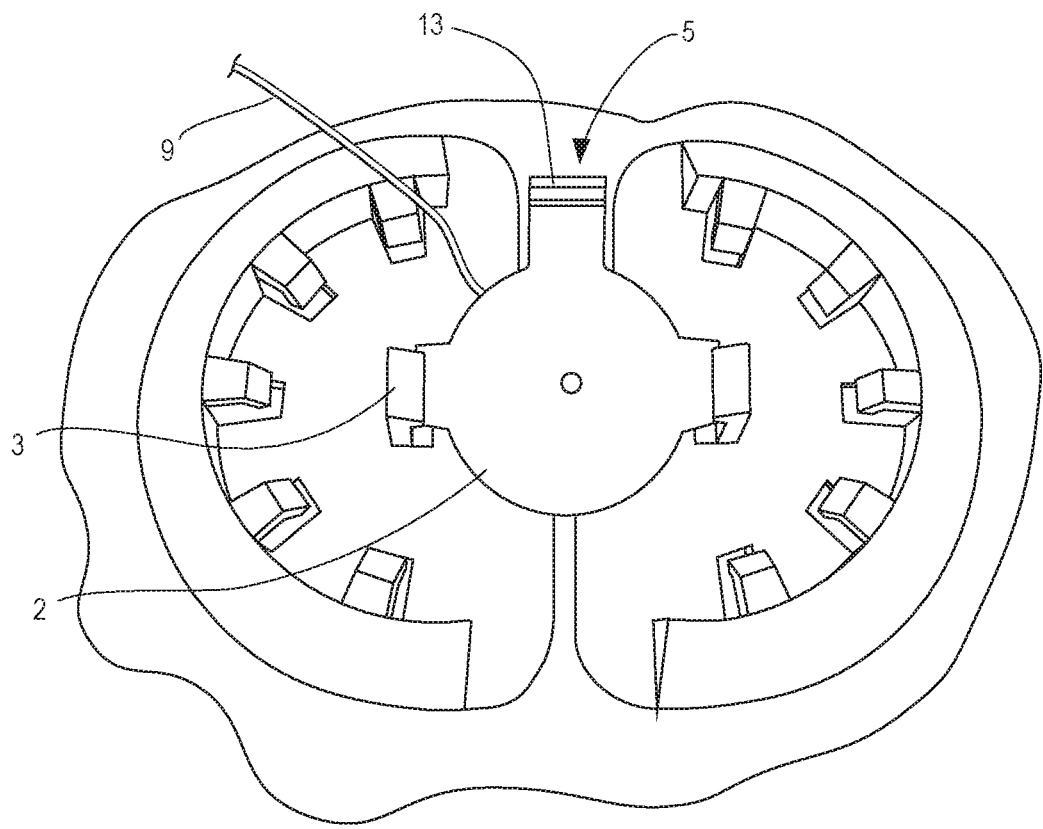
FIGS. 9A and 9B show an exemplary device of embodiments of the present disclosure with guide wires attached and secured and the locking tab closed.
Figure 9B:
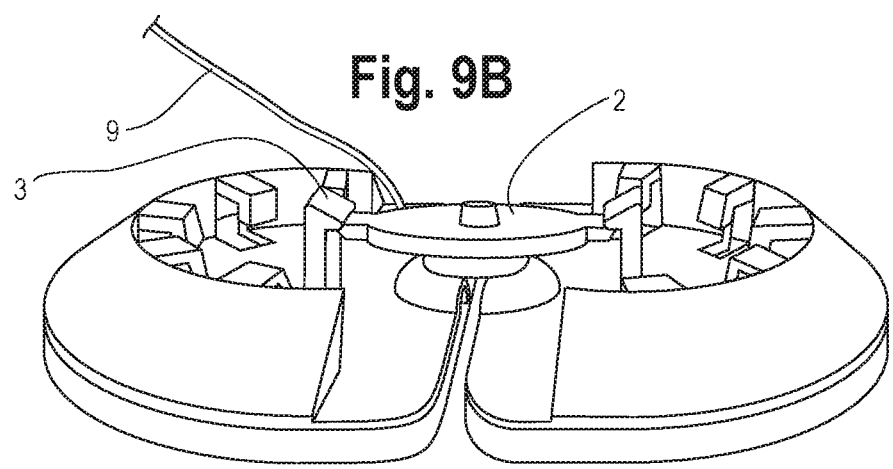

FIG. 9 shows guide wires 9 secured in an exemplary device. The locking tab 2 is closed and secured with locking clip 3, sealing the guide wires in the hole 10 in the locking tab insertion component 4. The left panel of FIG. 9 shows a top view of the closed device with guide wire 9 exiting the back lower section of the device, although other exit points are specifically contemplated. The right panel shows a side view of the closed device with the guide wire 9 exiting the back lower section of the device.

Figure 10:
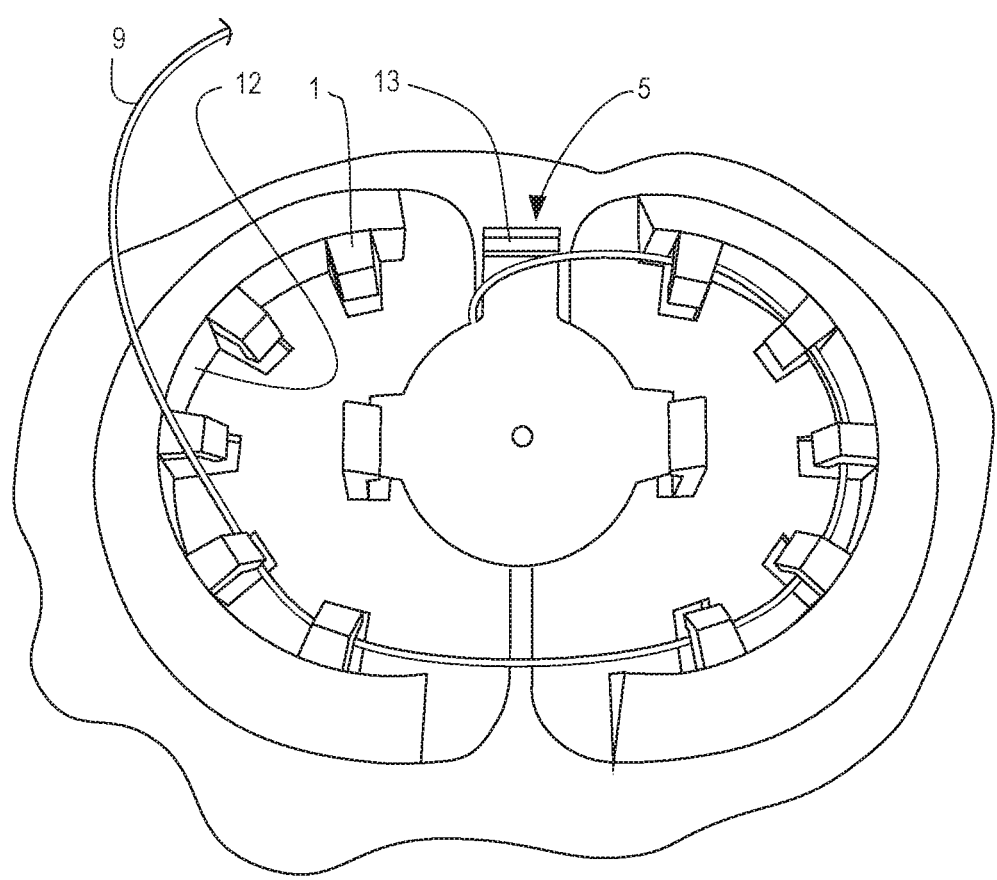
FIG. 10 shows an exemplary device of embodiments of the present disclosure with guide wires attached and secured and wrapped around the wire hooks.
Figure 11:
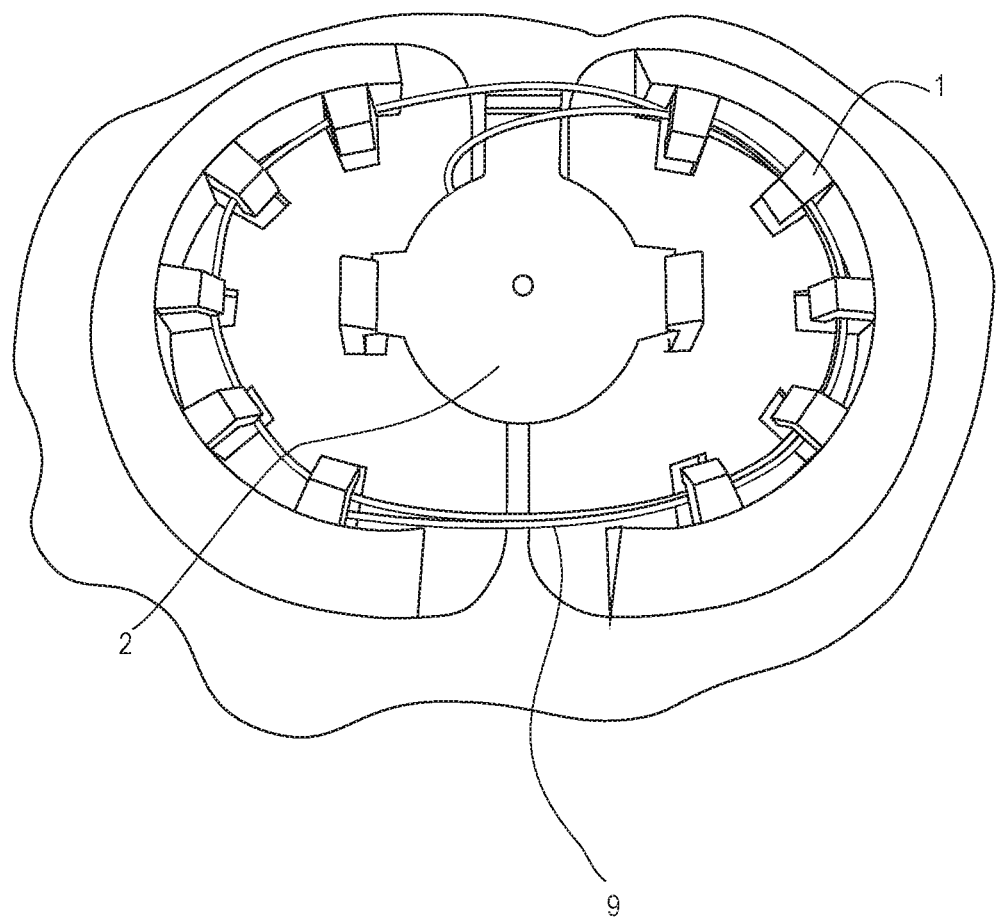
FIG. 11 shows an exemplary device of embodiments of the present disclosure with guide wires attached and secured and wrapped around the wire hooks.

FIG. 10 shows how guide wires 9 are secured in the closed device. After securing the guide wires 9 in the device, the guide wire 9 are wrapped in the grooved track 12 about wire hooks 1 to further secure the guide wires 9. FIG. 11 shows guide wires 9 fully secured on wire hooks 1. The patient is now free to move without the guide wires 9 dislodging or shifting.

Prior to surgery (e.g., in the pre-op or operating room), the guide wires 9 are removed from the device by removing guide wires 9 from the wire hooks 1, opening locking tab 2, and removing guide wires 9 from the hole in locking tab insertion component 4.

Devices described herein are constructed of any suitable material (e.g., polymers (e.g., polypropylene or polyethylene polymers), plastics, resins, etc.). In some embodiments, devices are fabricated from a mold or cast. In some embodiments, devices are injection molded or reaction injection molded, although other methods are specifically contemplated (e.g., vacuum (thermal) forming or compression molding).

The methods and devices described herein find use in securing guide wires for any number of non-limiting uses. In some embodiments, the guide wires are surgical guide wires (e.g., to identify a lump, lymph node (e.g., axilla, inguinal, or neck lymph nodes), soft tissue nodule, or suspected tumor). In some embodiments, the guide wires are used by surgeons to find non-palpable lumps for biopsy and/or lumpectomy (e.g., breast cancer or other tumors) located in any body part or tissue (e.g., chest wall, breast, abdomen, back, adipose tissue, muscle, lymph node, breast, etc.). Additional uses are specifically contemplated.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

I claim:

1. A guide wire securing device, comprising: a) wire retention and management component comprising a plurality of wire hooks and a grooved wire track formed by said wire hooks that passes through all of said wire hooks, b) a locking component positioned at a central portion of said device configured to secure a guide wire passed through said wire track to said central portion of said device, wherein said locking component comprises a locking tab, a locking tab insertion component configured to receive said locking tab, a living hinge configured to allow said locking tab to bend, a wire insertion groove comprising a wire hole and configured to receive said guide wire from said wire retention and management component, and a locking clop configured to secure said locking tab in the closed position, and c) an attachment component configured to secure said device to a subject, wherein said wire hooks are arranged in a circle or semi-circle around said locking component.

2. The device of claim 1, wherein said wire insertion groove is Y-shaped.

3. The device of claim 1, wherein said attachment component comprises adhesive attached to the back edge of said device.

4. The device of claim 1, wherein said attachment component comprises adhesive attached to a back edge of said device.

5. The device of claim 4, wherein said adhesive is foam adhesive.

6. The device of claim 1, wherein said device is fabricated from a polymeric material.

7. A system, comprising: a) a guide wire securing device, comprising: i) a wire retention and management component comprising a plurality of wire hooks and a grooved wire track formed by said wire hooks that passes through all of said wire hooks, ii) a locking component positioned at a central portion of said device configured to secure a guide wire passed through said wire track to said central portion of said device, wherein said locking component comprises a locking tab, a locking tab insertion component configured to receive said locking tab, a living hinge configured to allow said locking tab to bend, a wire insertion groove comprising a wire hole and configured to receive said guide wire from said wire retention and management component, and a locking clip configured to secure said locking tab in the closed position, and iii) an attachment component configured to secure said device to a subject, wherein said wire hooks are arranged in a circle or semi-circle around said locking component; and b) a guide wire inserted and secured therein.

8. The system of claim 7, wherein said guide wire is a surgical guide wire.

9. A method of securing a guide wire, comprising: a) contacting a guide wire inserted into a body part of a patient with a guide wire securing device, comprising: i) a wire retention and management component comprising a plurality of wire hooks and a grooved wire track formed by said wire hooks that passes through all of said wire hooks, ii) a locking component positioned at a central portion of said device configured to secure a guide wire passed through said wire track to said central portion of said device, wherein said locking component comprises a locking tab, a locking tab insertion component configure to receive said locking tab, a living hinge configured to allow said locking tab to bend, a wire insertion groove comprising a wire hole and configured to receive said guide wire from said wire retention and management component, and a locking clip configured to secure said locking tab in the closed position, and iii) an attachment component configured to secure said device to a subject, wherein said wire hooks are arranged in a circle or semi-circle around said locking component; b) inserting said guide wire through said wire retention and management component of said device; and c) securing said guide wire using said locking component.

10. The method of claim 9, wherein said guide wire is a surgical guide wire.

11. The method of claim 9, wherein said guide wire is a breast cancer guide wire that identifies a breast lump or tumor.

12. The method of claim 9, wherein said device is secured to said patient using said attachment component.

13. The method of claim 9, wherein said patient is pre-operative.

14. The method of claim 9, wherein said device is removed from said patient prior to said patient undergoing surgery.

15. The method of claim 14, wherein said surgery is biopsy or removal of a lump or nodule.

16. The method of claim 9, wherein said guide wire protrudes from said patient.

17. The method of claim 9, wherein said device facilitates rapid and easy wrapping and management of said guide wire.

* * * * *